US010470444B2

(12) United States Patent
Economides et al.

(10) Patent No.: US 10,470,444 B2
(45) Date of Patent: *Nov. 12, 2019

(54) METHOD FOR MAKING A GENETICALLY MODIFIED MOUSE WITH AN INDUCIBLE ACVR1 MUTATION THAT CAUSES ECTOPIC BONE FORMATION

(71) Applicant: Regeneron Pharmaceuticals, Inc., Tarrytown, NY (US)

(72) Inventors: Aris N. Economides, Tarrytown, NY (US); Sarah Jane Hatsell, Nyack, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/175,758

(22) Filed: Oct. 30, 2018

(65) Prior Publication Data

US 2019/0045760 A1    Feb. 14, 2019

Related U.S. Application Data

(63) Continuation of application No. 15/983,743, filed on May 18, 2018, which is a continuation of application
(Continued)

(51) Int. Cl.
*C12N 15/00* (2006.01)
*A01K 67/027* (2006.01)
(Continued)

(52) U.S. Cl.
CPC .......... *A01K 67/0275* (2013.01); *C07K 14/71* (2013.01); *A01K 2217/072* (2013.01);
(Continued)

(58) Field of Classification Search
USPC ............................................... 800/8, 18, 21
See application file for complete search history.

(56) References Cited

U.S. PATENT DOCUMENTS 7,205,148 B2 * 4/2007 Economides ...... A01K 67/0275
                                                        435/462
9,464,307 B2   10/2016 Horiuchi et al.
(Continued)

FOREIGN PATENT DOCUMENTS

CN       101313064 B    11/2012
WO    WO 00/063410 A1   10/2000
(Continued)

OTHER PUBLICATIONS

Cowan (Xenotransplantation, 2003, vol. 10, p. 223-231).*
(Continued)

*Primary Examiner* — Michael C Wilson
(74) *Attorney, Agent, or Firm* — Brian A. Cocca; Alston & Bird LLP

(57) ABSTRACT

A genetically modified mouse is provided that comprises a conditional Acvr1 allele that comprises a mutated exon that, upon induction, converts to a mutant exon phenotype, wherein the mutant exon phenotype includes ectopic bone formation. Mice comprising a mutant Acvr1 exon 5 in antisense orientation, flanked by site-specific recombinase recognition sites, are provided, wherein the mice further comprise a site-specific recombinase that recognizes the site-specific recombinase recognitions sites, wherein the recombinase is induced upon exposure of the mouse to tamoxifen. Upon exposure to tamoxifen, the recombinase is expressed and acts on the RRS-flanked mutant exon 5 and places the mutant exon 5 in sense orientation and deletes the wild-type exon.

21 Claims, 12 Drawing Sheets

Specification includes a Sequence Listing.

Related U.S. Application Data

No. 15/336,603, filed on Oct. 27, 2016, now Pat. No. 9,999,207, which is a continuation of application No. 14/207,320, filed on Mar. 12, 2014, now Pat. No. 9,510,569.

(60) Provisional application No. 61/778,814, filed on Mar. 13, 2013.

(51) Int. Cl.
*C07K 14/71* (2006.01)
*C12N 15/85* (2006.01)

(52) U.S. Cl.
CPC .. *A01K 2217/203* (2013.01); *A01K 2227/105* (2013.01); *A01K 2267/0306* (2013.01); *C12N 2015/8536* (2013.01); *C12N 2800/30* (2013.01)

(56) References Cited

U.S. PATENT DOCUMENTS

| | | | |
|---|---|---|---|
| 9,510,569 B2* | 12/2016 | Economides | A01K 67/0275 |
| 9,999,207 B2* | 6/2018 | Economides | A01K 67/0275 |
| 10,023,916 B2 | 7/2018 | Economides et al. | |
| 2006/0179501 A1* | 8/2006 | Chan | A01K 67/0275 800/18 |
| 2007/0204353 A1 | 8/2007 | Joyner et al. | |
| 2018/0263227 A1 | 9/2018 | Economides et al. | |
| 2019/0053473 A1 | 2/2019 | Economides et al. | |

FOREIGN PATENT DOCUMENTS

| | | |
|---|---|---|
| WO | WO 02/088353 A2 | 7/2002 |
| WO | WO 02/088353 A3 | 7/2002 |
| WO | WO 07/123896 A2 | 11/2007 |
| WO | WO 11/059799 A1 | 5/2011 |
| WO | WO 14/160429 A1 | 10/2014 |

OTHER PUBLICATIONS

Ageta-Ishahara (Molecular Brain, 2013, 6:35, p. 1-14).*
Chakkalakal, J. Bone and Mineral Res. Aug. 2012, vol. 27, p. 1746-1756.*
Indra (Nucleic Acids Res., 1999, vol. 27, No. 22, p. 4324-4327).*
Ageta-Ishahara et al., "Chronic overload of SEPT4, a parkin substrate that aggregates in Parkinson's disease, causes behavioral alterations but not neurodegeneration in mice," Molecular Brain, 6:35, pp. 1-14, (2013).
Chakkalakal, et al., "An Acvr1 R206H Knock-in Mouse Has Fibrodysplasia Ossificans Progressiva.," Journal of Bone and Mineral Research, 27(8):1746-1756, (2012).
Cowan et al., "Targeting gene expression to endothelium in transgenic animals: a comparison of the human ICAM-2, PECAM-1and endoglin promoters," Xenotransplantation, 10:223-231, (2003).
EP 18150822.7 Extended Search Report dated Mar. 26, 2018.
Feil et al., "TRegulation of Cre Recombinased Activity by Mutated Estrogen Receptor Ligand-Binding Domains," Biochemical and Biophysical Research Communications, 237:752-757, (1997).
Fukuda et al., "Generation of a mouse with conditionally activated signaling through the BMP receptor, ALK2" Genesis, 44:159-167, (2006).
Glaser et al., "In vivo somatic cell gene transfer of an engineered Noggin mutein prevents BMP4-induced heterotopic ossification," J Bone Joint Surg Am, 85-A(12):2332-2342, (2003).
Hatsell, et al., "ACVR1R206H receptor mutation causes fibrodysplasia offificans progressiva by imparting responsiveness to activin A," retrieved online at http://stm.sciencemag.org/content/7/303/303ra137, vol. 7, Issue 303, (Sep. 2, 2015).
Holkers et al., "Nonspaced inverted DNA repeats are preferential targets for homology-directed gene repair in mammalian cells," Nucleic Acids Research, 40(5):1984-1999, (2012). Published online Nov. 12, 2011.
Indra et al., "Temporally-controlled site-specific mutagenesis in the basal layer of the epidermis: compariston of the recombinase activity of the tamoxifin-inducible Cre-ERT and Cre-ERT2 recombinases," Nucleic Acids Research, 27(22):S4324-4327, (1999).
Kan et al., "Animal Models of Typical Heterotopic Ossification," Journal of Biomedicine and Biotechnology, doi:10.1155/2011/309, vol. 2011, Article ID 309287, 8 pages (2011).
Kan et al., "Transgenic Mice Overexpressing BMP4 Develop a Fibrodysplasia Ossificans Progressiva (FOP)-Like Phenotype," American Journal of Pathology, 65(4):1107-1115, (2004).
Kaplan, et al., Fibrodysplasia ossificans progressive: mechanisms and models of skeletal metamorphosis, Disease Models & Mechanisms, 5:756-762, (2012).
Mishina et al., "Multiple Roles for Activin-Like Kinase-2 Signaling during Mouse Embryogenesis," Developmental Biology, 213:314-326, (1999).
Pignolo et al., "Fibrodysplasia ossificans Progressiva: Clinical and Genetic Aspects," Orphanet Journal of Rare Diseases, 6(8):1-6, (2011).
Rybchin, Basics of genetic engineering, Textbook for High Schools, Saint-Petersburg, Publishing House SPbSTU, 522: 410-417, (2002).
Schnutgen et al., "A directional strategy for monitoring Cre-mediated recombination at the cellular level in the mouse," Nature Biotechnology, 21:562-565, (2003).
Shore et al., "A recurrent mutation in the BMP type I receptor ACVR1 causes inherited and sporadic fibrodysplasia ossificans progressiya," Nature Genetics, 38(5):525-527, (2006).
Stoeger et al., "In situ gene expression analysis during BMP2-induced ectopic bone formation in mice shows simultaneous endochondral and intramembranouse ossification," Growth Factors, 20(4):197-210, (2002).
U.S. Appl. No. 14/207,320, Non-Final Office Action dated May 5, 2015.
U.S. Appl. No. 14/207,320, Notice of Allowance dated Jul. 28, 2016.
U.S. Appl. No. 14/207,320, Requirement for Retriction/Election dated Feb. 24, 2015.
U.S. Appl. No. 15/336,603, Non-Final Office Action dated Sep. 5, 2017.
U.S. Appl. No. 15/336,603, Notice of Allowance dated Feb. 21, 2018.
U.S. Appl. No. 15/336,603, Requirement for Restriction/Election dated Jun. 21, 2017.
WIPO Application No. PCT/US2014/026582, PCT International Search Report and Written Opinion of the International Searching Authority dated Aug. 4, 2014.
WIPO Application No. PCT/US2014/026582, PCT International Preliminary Report on Patentability dated Sep. 24, 2015.
Yu, et al., "BMP type I receptor inhibition reduces heterotopic ossification," Nature Medicine, vol. 14 No. 12 pp. 1363-1369 (Dec. 2008).
U.S. Appl. No. 15/983,743, Non-Final Office Action dated Jan. 30, 2019.
U.S. Appl. No. 16/175,762, Non-Final Office Action dated Jan. 30, 2019.

* cited by examiner

Table 5. Primers and Probes for Genotyping Genetically Modified Mice

| Name | Target | Assay ID | Parameter Set | Primer or Probe Forward Primer | Strand or Label | 5Pos | 3Pos | Length | Tm |
|---|---|---|---|---|---|---|---|---|---|
| Acvr1 i5 TU | S13080836 | 51 | Most Restrictive v2.0 | GGCTGACTGA TCTGAAGGAA ATGG | S | 175 | 198 | 24 | 66.94 |
| Acvr1 i5 TD | S13081203 | 6 | Less Restrictive v2.0 | TGAAGGAAAT GGGCTTCTGG ATAG | S | 4 | 27 | 24 | 67.16 |
| | | | | Reverse Primer | | | | | |
| Acvr1 i5 TU | S13080836 | 51 | Most Restrictive v2.0 | AGAGGAAGGA GACGCTAAGA ATC | AS | 260 | 238 | 23 | 65.4 |
| Acvr1 i5 TD | S13080836 | 6 | Less Restrictive v2.0 | CATACTCACT CTTCCTGTTA GAGGA | AS | 96 | 72 | 25 | 65.71 |
| | | | | Probe | Labeling | Strand | 5Pos | 3Pos | Length | TM |
| Acvr1 i5 TU | S13080836 | 51 | Most Restrictive v2.0 | TCTGGATAGT AAGGTCAGTT GCTGCG | FAM-BHQ-1 | S | 202 | 227 | 26 | 69.57 |
| Acvr1 i5 TD | S13080836 | 6 | Less Restrictive v2.0 | AAGGTCAGTT GCTGCGTCTT CCC | FAM-BHQ-1 | S | 29 | 51 | 23 | 69.81 |

FIG. 12

METHOD FOR MAKING A GENETICALLY MODIFIED MOUSE WITH AN INDUCIBLE ACVR1 MUTATION THAT CAUSES ECTOPIC BONE FORMATION

CROSS-REFERENCE TO RELATED APPLICATION

The present application is a continuation of U.S. application Ser. No. 15/983,743 filed May 18, 2018, which is a continuation of U.S. application Ser. No. 15/336,603 filed Oct. 27, 2016, now U.S. Pat. No. 9,999,207, which is a continuation of U.S. application Ser. No. 14/207,320 filed Mar. 12, 2014, now U.S. Pat. No. 9,510,569, which claims priority from U.S. Provisional Application No. 61/778,814 filed Mar. 13, 2013, each incorporated by reference in its entirety for all purposes.

REFERENCE TO A SEQUENCE LISTING

The application refers to sequences written in the file 522468_SEQLST.txt, created on, Oct. 30, 2018, which is 1,440 bytes, which is incorporated by reference.

FIELD

Genetically modified non-human animals that have a mutant allele of an Acvr1 gene; nucleic acid constructs that comprise conditional mutants of an Acvr1 gene; non-human animals that exhibit a phenotypical feature of fibrodysplasia ossificans progressiva (FOP). Genetically modified mice that exhibit ectopic bone formation. Non-human animals containing conditional mutant ACRV1 alleles that are expressed ex utero but not in utero.

BACKGROUND

Acrv1 is a type I receptor for bone morphogenic proteins (BMPs). Certain mutations in the human Acvr1 gene, including mutations that give rise to the amino acid modification R206H mutation, are strongly associated with the disease fibrodysplasia ossificans progressiva (FOP) (see, e.g., US Pat. Appl. Publ. No. 2009/0253132; see also, Pignolo, R. J. (2011) Fibrodysplasia Ossificans Progressiva: Clinical and Genetic Aspects, Orphanet Journal of Rare Diseases, 6:80, 1-6). The R206H mutation, among others, is believed to increase sensitivity of the receptor to activation and render it more resistant to silencing. Chimeric mice that bear an R206H mutation in Acvr1 develop an FOP-like phenotype (see, e.g., Chakkalakal et al. (2012) An Acvr1 R206H knock-in mouse has fibrodysplasia ossificans progressiva, J. Bone and Mineral Res. 27:1746-1756).

Certain mutations in the Acvr1, e.g., those resulting in an R206H Acvr1 protein mutation, are perinatal lethal in mice. Where a mutation is perinatal lethal, it is not possible to pass a knock-in gene comprising the mutation through the germline of a non-human animal. For example, the above-mentioned studies required working with chimeric mice that possess in some cells the indicated mutation but that are unable to transmit the mutation in the germline; thus, a stable and useful mouse line has not been established that comprises the R206H mutation in the germline. There remains a need for non-human animals that can transmit an ACRV1 mutation that is perinatal or embryonic lethal in the germline to produce progeny that are useful, e.g., to produce a non-human animal that exhibits a phenotype associated with the ACRV1 mutation, e.g. FOP, an FOP feature, or a feature of a related disorder, or a related disorder.

SUMMARY

Genetically modified non-human animals are provided that comprise in their germline a nucleic acid sequence that comprises a modification of an Acvr1 gene.

Genetically modified non-human animals are provided that comprise in their germline a nucleic acid sequence that comprises a conditional genetic modification of an Acvr1 gene, wherein the genetic modification renders the non-human animal susceptible to ectopic bone formation.

Genetically modified non-human animals are provided that comprise in their germline a nucleic acid sequence that comprises a conditional genetic modification comprising a conditional mutant Acvr1 exon, wherein induction of expression of the conditional mutant Acvr1 exon confers upon the non-human animal a susceptibility to ectopic bone formation. In one embodiment, the mutant Acvr1 exon is exon 5. In a specific embodiment, the mutation expresses an Acvr1-encoded protein having an exon 5 with a R2026H mutation.

Non-human animals are provided that conditionally express a mutant Acvr1 allele. In various aspects, the mutant Acvr1 allele is an allele that confers a pathological phenotype on the non-human animal expressing the allele. In various aspects, the non-human animals comprise a mutant exon of an Acvr1 allele flanked upstream and downstream with site-specific recombinase recognition sites (SRRS's), and the non-human animal comprises a recombinase that recognizes the SRRS's, wherein the recombinase is inducible.

Non-human animals are provided that comprise a modification of an Acvr1 allele that causes (in one embodiment, in a heterozygote; in one embodiment, in a homozygote), promotes, or makes the non-human animal susceptible to ectopic ossification.

Non-human animals are provided that comprise a conditional mutation of an Acvr1 allele, wherein the mutant Acvr1 allele is not expressed in utero, and is not expressed perinatally, and wherein the non-human animals express the mutant Acvr1 allele in a conditional manner, wherein the conditional expression is induced by administration of a compound of interest to the non-human animal.

Acvr1 loci are provided that comprise a modification that comprises a conditional mutant exon, wherein the conditional mutant exon is expressed upon an experimentally-induced induction.

In one aspect, a genetically modified Acvr1 locus is provided, comprising a mutant exon in antisense orientation, flanked upstream and downstream by SRRS's. In one embodiment, the locus is present in a non-human animal that further comprises an inducible recombinase gene that recognizes the SRRS's that flank the mutant exon.

In one aspect, a non-human animal is provided that comprises a modified Acvr1 locus comprising a mutant exon in antisense orientation, wherein the mutant exon is flanked upstream and downstream by SRRS's that are oriented to direct an inversion when acted upon by a recombinase that recognizes the SRRS's. In one embodiment, the mutant exon upon inversion replaces the corresponding wild-type exon of the Acvr1 locus. In one embodiment, the non-human animal further comprises an inducible recombinase gene, wherein the recombinase of the inducible recombinase gene recognizes the SRRS's. In a specific embodiment, the SRRS's are lox sites or variants thereof, the recombinase is Cre, and the recombinase is inducible by tamoxifen. In a specific embodiment, the recombinase is a Cre-ER$^{T2}$. In one embodiment, the non-human animal is a rodent, e.g., a mouse or rat. In a specific embodiment, the rodent is a rat, and the mutant Acvr1 exon is exon 5.

In one aspect, a genetically modified mouse is provided that comprises a nucleic acid construct comprising a mutant exon 5 (e5) encoding an R206H mutation, wherein the mutant e5 is present in antisense orientation and is flanked upstream and downstream by SRRSs oriented to direct an inversion of the mutant e5; and the mouse comprises an inducible recombinase gene encoding a recombinase that is capable of inverting the antisense mutant e5 exon to sense orientation.

In one aspect, a genetically modified mouse is provided that comprises a nucleic acid construct at an Acvr1 locus in the germline of the mouse, wherein the nucleic acid construct comprises, with respect to the direction of transcription of the Acvr1 gene, a construct comprising a wild-type e5 gene in sense orientation and a mutant e5 allele in antisense orientation, wherein upstream of the wild-type e5 allele is a first SRRS (SRRS1) that is compatible with a second SRRS (SRRS2) located just downstream (with respect to transcriptional direction of the Acvr1 gene) of the antisense mutant e5, wherein SRRS1 and SRRS2 are oriented to direct an inversion. The construct further comprises a third SRRS (SRRS3) disposed between the wild-type e5 and the mutant antisense e5, and the construct further comprises a fourth SRRS (SRRS4) that is compatible with SRRS3, and which is located downstream (with respect to the direction of orientation of the Acvr1 gene) of SRRS2, wherein SRRS3 and SRRS4 are oriented to direct an inversion. Each SRRS (1-4) is recognized by the same inducible recombinase.

In one embodiment, the inducible recombinase is in the germline of the mouse.

In one embodiment, the SRRS sites are recognizable by a Cre recombinase.

In one embodiment, SRRS1 and SRRS2 are lox2372 sites; SRRS3 and SRRS are loxP sites, and the inducible recombinase is a CreER$^{T2}$ (see, e.g., FIG. 1).

In one embodiment, SRRS1 and SRRS2 are loxP sites; SRRS3 and SRRS4 are lox2372 sites, and the inducible recombinase is a CreER$^{T2}$ (see, e.g., FIG. 1).

In one embodiment, the CreER$^{T2}$ is present at the ROSA26 locus (e.g., Gt(ROSA26)Sor$^{CreERT2/+}$.

In one aspect, a genetically modified mouse is provided comprising the genotype Acvr1$^{[R206H]COIN/+}$; Gt(ROSA26)Sor$^{CreERt2/+}$.

In one aspect, a genetically modified rodent is provided that expresses a normal Acvr1 exon 5 in utero and perinatally, wherein upon treatment of the genetically modified rodent with a recombinase, the mouse expresses an Acvr1-encoded protein that comprises a mutation encoded by exon 5. In one embodiment, the mutation is an exon 5 mutation that encodes a R206H mutation.

In one aspect, an adult rodent is provided that expresses a mutant Acvr1 gene product characterized by a R206H modification, wherein at least 99% of the cells of the mouse comprise a mutant Acvr1 gene encoding the R206H modification.

In one aspect, a genetically modified rodent is provided that comprises a mutant Acvr1 gene product characterized by a R206H modification, wherein the mutant Acvr1 gene is present in at least 90%, 95%, 96%, 97%, 98%, or 99% or more of the cells of the genetically modified rodent.

In one aspect, a genetically modified rodent is provided, wherein the rodent comprises an Acvr1 locus in its germline that, upon exposure to a recombinase, expresses a protein encoded by the Acvr1 locus that comprises a R206H modification.

In one aspect, a rodent is provided that expresses a mutant protein comprising a R206H mutation, wherein the mouse is non-chimeric. In one embodiment, the extent of chimerism of the rodent is no more than 1%.

In one aspect, a mouse is provided that expresses a mutant protein from a modified Acvr1 locus in the germline of the mouse, wherein all Acvr1-expressing cells of the mouse comprise a modified Acvr1 gene that encodes an Acvr1 protein that comprises an R206H modification. In one embodiment, all germ cells of the mouse comprise a modified Acvr1 locus comprising a conditional genetic modification that encodes an Acvr1 protein with an R206H modification.

In one aspect, a genetically modified mouse comprising an engineered Acv1$^{[R206H]COIN}$ allele is provided, wherein the first codon of human ACVR1 exon 5 (isoform 003) is modified encode an E, wherein at the protein level the humanized exon is identical to the wild type mouse Acv1 exon 5 (isoform 001).

In one aspect, a mouse is provided that comprises a conditional genetic modification of an Acvr1 gene, wherein the modification changes an amino acid in an ACVR1 α-helix comprising ACVR1 amino acids 198-206 and results in a constitutive activation of the protein encoded by the Acvr1 locus.

In one embodiment, the conditional genetic modification is in an amino acid selected from amino acid 198, 199, 200, 201, 202, 203, 204, 205, 206, and a combination thereof. In a specific embodiment, the amino acid is 206, and the modification is a nucleotide change that forms a codon for histidine.

In one embodiment, the mouse is heterozygous for the conditional genetic modification. In one embodiment, the mouse is homozygous for the conditional genetic modification.

In various aspects, the non-human animal is a mammal. In one embodiment, the mammal is a rodent. In one embodiment, the rodent is selected from the group consisting of a mouse, a rat, and a hamster. In a specific embodiment, the rodent is a mouse.

In various aspects, the genetically modified non-human animal comprises an array of SRRS's that are arranged to direct a deletion of a wild-type Acvr1 exon 5 and place a mutant exon 5 from an antisense orientation to a sense orientation.

In various aspects, the genetically modified non-human animal further comprises an inducible recombinase that acts upon a nucleic acid construct in the Acvr1 locus to remove the wild-type exon and replace it with the mutant exon. In one embodiment, the inducible recombinase is CreER$^{T2}$.

In various aspects, the genetically modified non-human animals, upon expression of the mutant Acvr1 allele, are capable of expressing the alternate (wild-type) allele.

In various aspects, the genetically modified non-human animal that expresses the mutant Acvr1 allele is a model for an ectopic ossification disorder. In one embodiment, the ectopic ossification disorder is fibrodysplasia ossificans progressiva (FOP).

In various aspects, genetically modified non-human animals are provided that conditionally express a mutant Acvr1 allele comprising a mutant exon 5 (e.g., expressing a protein comprising an R206H mutation) upon exposure to tamoxifen, wherein the non-human animals comprise a tamoxifen-inducible recombinase that converts a wild-type exon 5 to a mutant exon 5 within the Acvr1 gene.

BRIEF DESCRIPTION OF THE DRAWINGS

FIG. 12 illustrates primers and probes used in a loss of allele assay to genotype genetically modified mice compris-ing the conditional mutation in the Acvr1 gene; SEQ ID NOs are, from top to bottom: for the forward primer from top to bottom SEQ ID NO:1, SEQ ID NO:2; for the reverse primer from top to bottom SEQ ID NO:3, SEQ ID NO:4; for the probe SEQ ID NO:5, SEQ ID NO:6.

DETAILED DESCRIPTION

Figure 1:
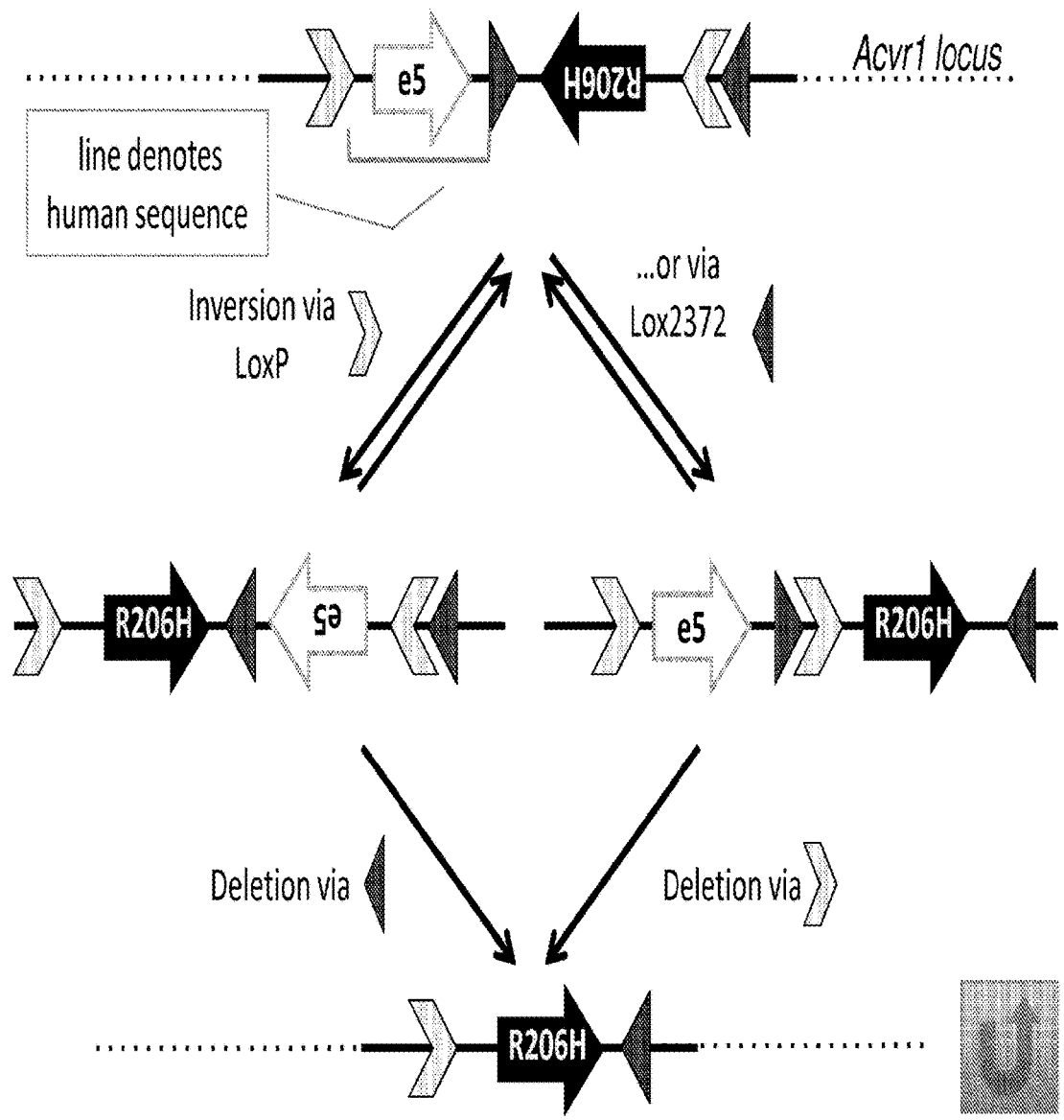
FIG. 1 illustrates design of a conditional allele at an Acvr1 locus that converts, e.g., a mouse Acvr1 exon 5 to a human R206H exon using loxp and lox2372 sites.

Fibrodysplasia ossificans progressiva (FOP) is an autosomal dominant disorder of ectopic bone formation. Linkage studies in affected families reveal that the FOP gene maps to chromosome 2q23-24 where a 617G-to-A mutation (R206-to-H) in the activation domain of activin A type I receptor gene (Acvr1) was found on all affected individuals examined in the studies (Shore et al., (2006) A recurrent mutation in the BMP type I receptor Acvr1 causes inherited and sporadic fibrodysplasia ossificans progressiva, Nat. Genet. 38:525-527), consistent with FOP being caused by constitutive activation of Acvr1 (Id.).

Genetically modified mice are provided that express an Acvr1 protein comprising a modification that results in a disorder characterized by ectopic bone formation, e.g., FOP. Mice expressing the modified Acvr1 protein include mice that are not chimeric, e.g., mice whose genomes carry a (conditional) modification of the Acvr1 protein that results in ectopic bone formation in a mouse that expresses the modified Acvr1 protein.

Certain mutations in the Acvr1 protein, e.g., the FOP-associated R206H mutation, are difficult if not impossible to create in the germline of mice due to embryonic or perinatal fatality associated with the mutation. Genetically modified mice are provided that comprise an COnditional-by-INversion (COIN) design that provides for a conditional inversion and removal of a wild-type exon and replacement of the wild-type exon with a mutant exon. This COIN design allows for forming a conditional allele by placement of a nucleic acid sequence encoding an inverted mutant exon to be placed next to a wild-type exon to be deleted. Through selection of recombinase recognition sites (RRS's), the inverted mutant exon is reversed to place it in reading frame whereas the wild-type exon is deleted. This COIN approach relies on the placement of incompatible RSS's (e.g., lox2372 and loxp) surrounding the wild-type and mutant exons. This COIN approach thus does not allow for expression of the (perinatal/embryonic) lethal mutation unless the COIN allele is acted upon by the selected recombinase(s). Another advantage of this COIN approach is permanent removal of the wild-type exon upon exposure to the selected recombinase, and thus no inverted repeat remains in the genome post-inversion. This is advantageous because it eliminates the possibility of re-inversion, because the remaining recombinase sites are incompatible (e.g., lox2372 and loxP). In this instance, humanization of the wild-type mouse exon also minimizes inverted repeat sequence, thus facilitating cloning steps and alleviating concerns of rearrangements during and after targeting.

If a mouse bearing the COIN allele is bred to a recombinase-containing mouse, the (perinatal/embryonic) lethal mutation will express in the progeny in utero, thus confounding the goal of making an animal that can be studied which expresses the allele. Therefore, the mouse bearing the COIN allele is not bred with an unregulated recombinase-containing mouse. Instead, the mouse is bred with a mouse that contains a Cre-ER protein that this modified with T2 mutations (a Cre-ER$^{T2}$ mouse), or modified to contain a Cre-ER$^{T2}$ allele. The Cre-ER$^{T2}$ protein is a Cre protein modified with an estrogen receptor sequence that comprises T2 mutations that render the Cre protein inactive (see, Indra, A. et al. (1999) Temporally-controlled site-specific mutagenesis in the basal layer of the epidermis: comparison of the recombinase activity of the tamoxifen-inducible Cre-ER$^T$ and Cre-ER$^{T2}$ recombinases, Nucleic Acids Res. 27(22): 4324-4327; Feil, R. et al. (1997) Regulation of Cre Recombinase Activity by Mutated Estrogen Receptor Ligand-Binding Domains, Biochem. Biophys. Res. Commun. 237: 752-757; U.S. Pat. No. 7,112,715). A mouse comprising a conditional allele constructed with Cre-responsive RSS's as described herein, and containing a Cre-ER$^{T2}$ allele, would therefore express the wild-type allele unless and until the mouse was exposed to tamoxifen to induce Cre activity. In this way, mice are made that contain a mutant Acvr1 allele in their germline but that do not express a mutant Acvr1 protein unless and until the mice are exposed to tamoxifen. Following exposure to tamoxifen, the Cre-ER$^{T2}$ fusion protein is activated and the conditional allele converts to a mutant allele and, in various embodiments, the conversion to the mutant allele is irreversible, with deletion of the wild-type allele. In this manner, a mouse line containing an otherwise lethal Acvr1 mutation can be maintained essentially indefinitely, producing the desired genetic lesion and accompanying phenotype whenever desired. In various embodiments, a genetically modified mouse comprising the Acvr1 COIN allele is made by modifying a mouse ES cell to contain the COIN allele, and modifying the same ES cell to contain a gene encoding the tamoxifen-inducible Cre-ER$^T$ or Cre-ER$^{T2}$, and using the ES cell as a donor cell to make a mouse that contains the COIN allele and the modified Cre gene. All of the references cited herein are hereby incorporated by reference.

Engineering a Conditional ACVR1 Allele that is Germline Transmissible

In order to engineer a mouse model of Fibrodysplasia Ossificans Progressiva (FOP), the R206H "classic FOP" mutation of human Acvr1 (Shore et al. (2006)) was engineered into the corresponding mouse gene, Acvr1. This mutation has already been modeled non-conditionally in the mouse, but the resulting chimeric mice (arising from blastocyst microinjection of the targeted ES cells) were unable to transmit the mutation through the germline, presumably due to embryonic or perinatal lethality (Chakkalakal, S. A. et al. (2012) An Acvr1 R206H knock-in mouse had fibrodysplasia ossificans progressiva, J. Bone and Mineral Res. 27:1746-1756). Prior to knowledge of this phenotype, and based on the phenotype of Acvr1 homozygous-null mice, which reveals a profound role of Acvr1 during development (Mishina et al. (1999) Multiple roles for activin-like kinase-2 signaling during mouse embryogenesis, Dev. Biol. 212:314-326), it was decided to engineer the Acvr1$^{[R206H]}$ mutation in a conditional manner in the mouse, utilizing a variation on FIEx (Schnutgen, F. et al. (2003) A directional strategy for monitoring Cre-mediated recombination at the cellular level in the mouse, Nat. Biotech. 21:562-565) and COIN (U.S. Pat. No. 7,205,148) methodologies.

Figure 2:
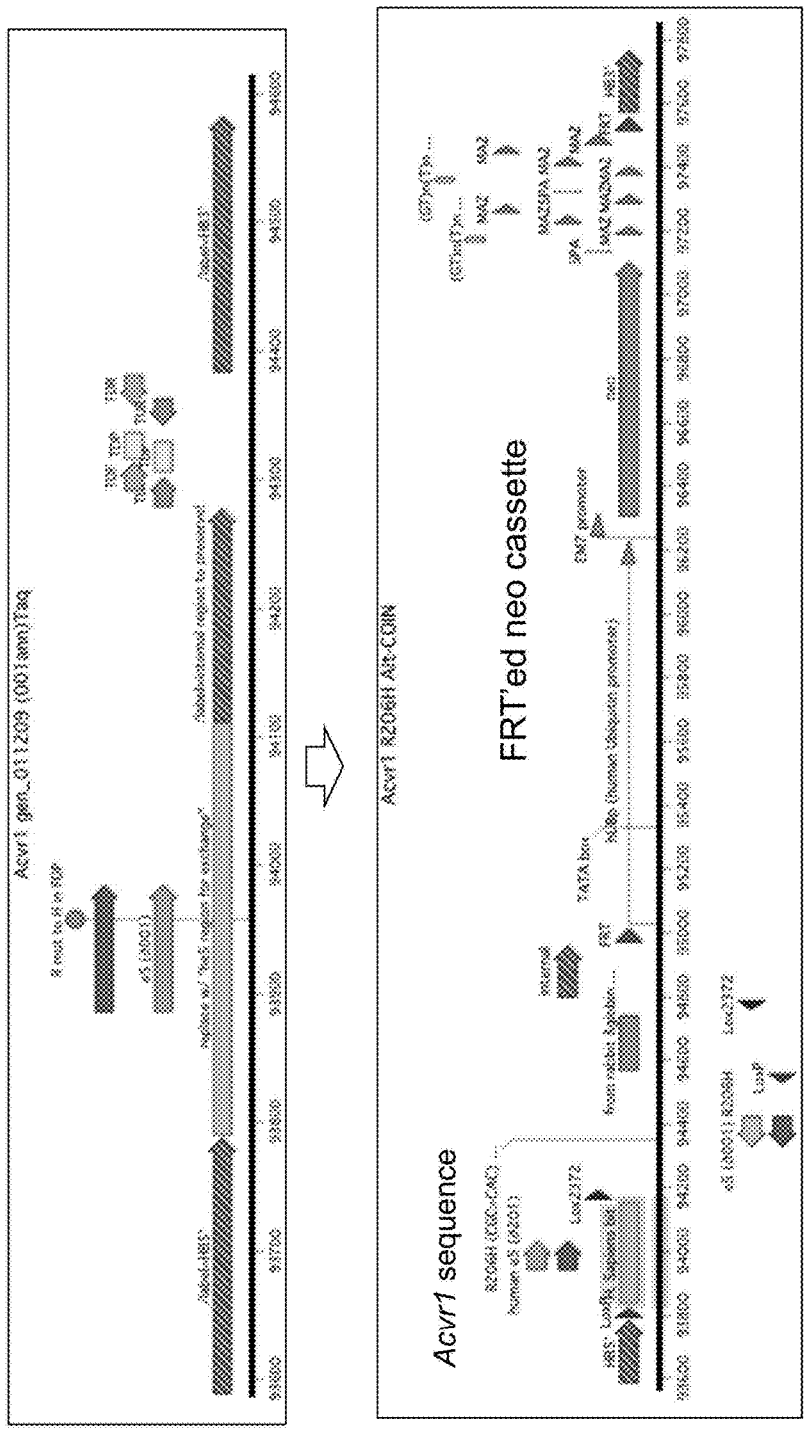
FIG. 2 illustrates design of a conditional allele of Acvr1 R206H classic FOP mutant receptor gene. Mouse Exon 5 (e5 in isoform 001) is replaced with human exon 5 (in human ACVR1 isoform 003); a mouse mutant exon is simultaneously introduced in the antisense strand, together with a FRT'ed selection cassette (hUB-Neo); human e5 is flanked with loxP and lox2372 pointing East, and another loxP and Lox2372 sites are placed downstream of mouse e5(R206H) and deletion of the human e5, upon exposure to Cre, as detailed schematically in FIG. 1.
Figure 3:
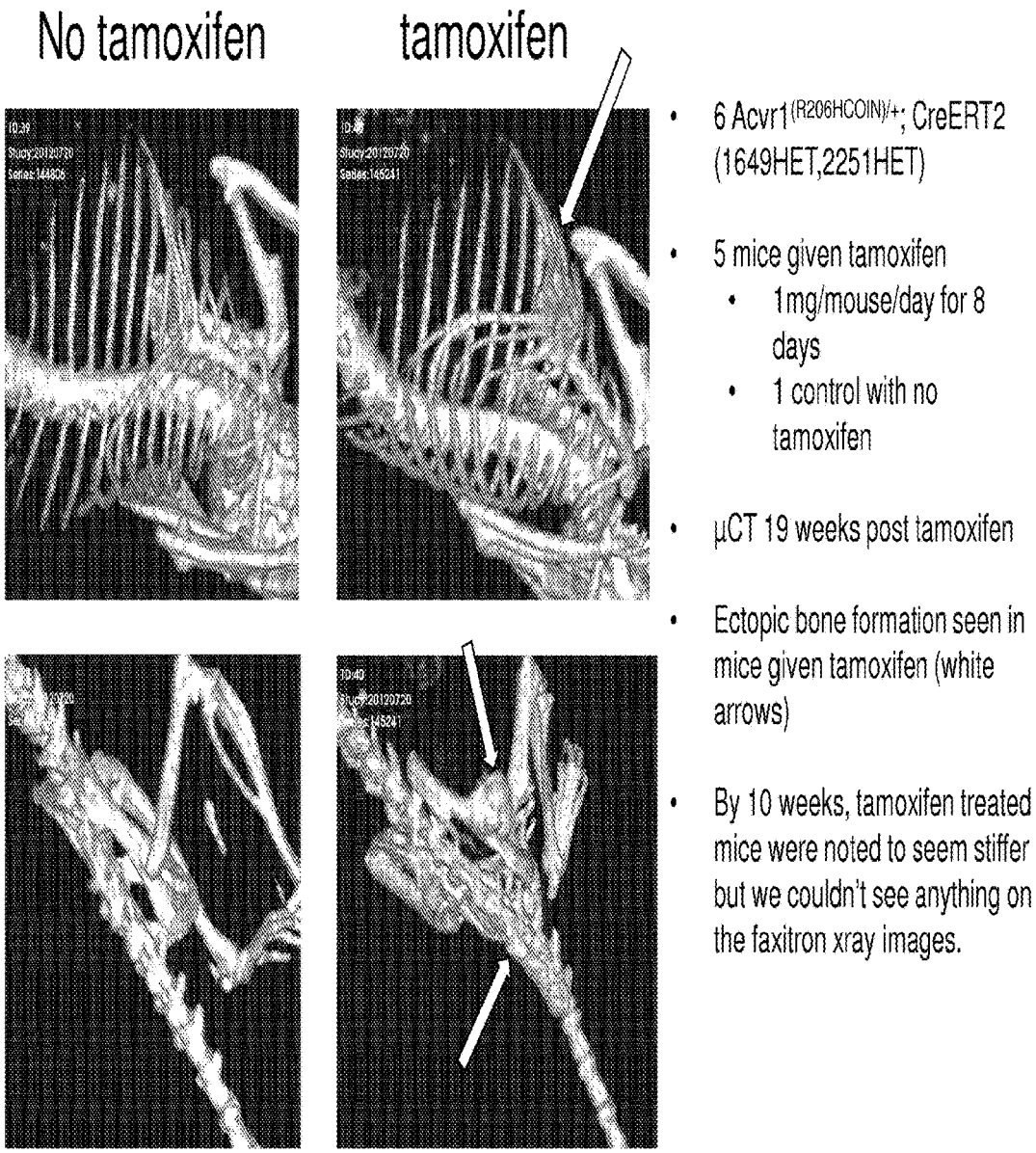
FIG. 3 illustrates activation of the Acvr1$^{[R206H]COIN}$ allele results in an FOP-like phenotype in mice genetically modified with the conditional allele.
Figure 4:
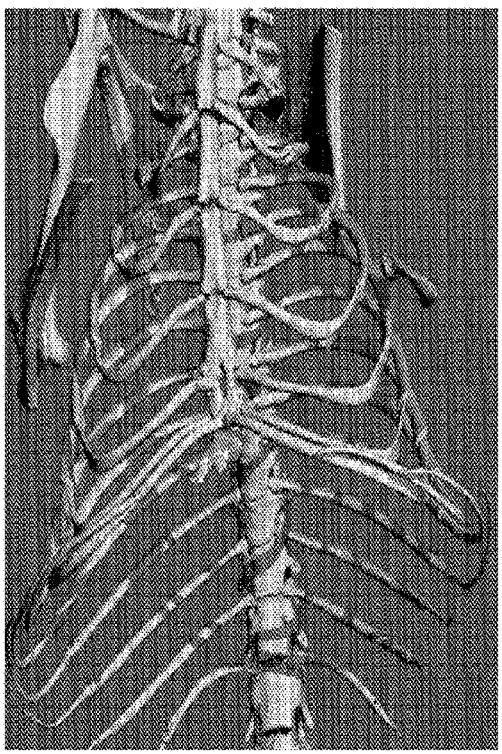
FIG. 4 illustrates ectopic bone formation in genetically modified mice comprising the conditional allele induced in mice administered tamoxifen; an example of ectopic bone formation at the sternum is indicated in the right panel with white arrows. In the absence of tamoxifen (left panel), no ectopic bone formation is detected.
Figure 4:
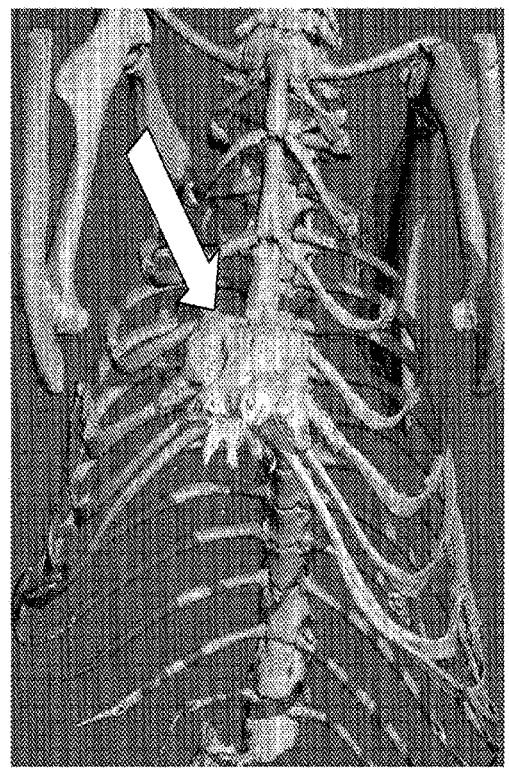
Figure 5:
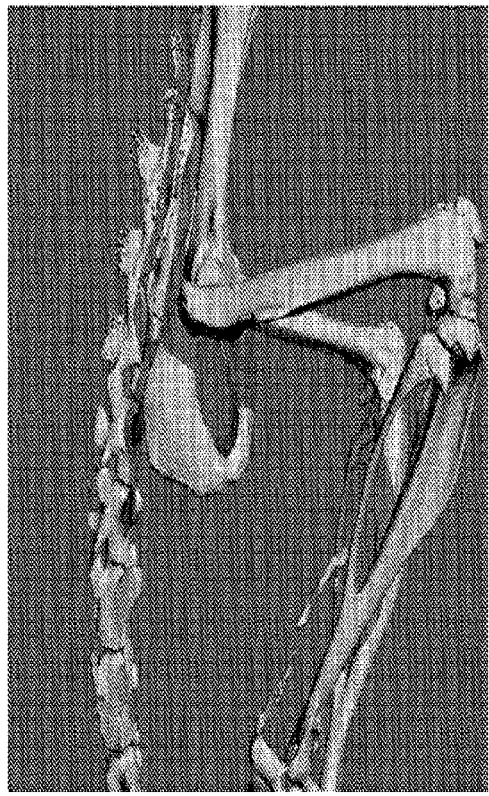
FIG. 5 provides another illustration of ectopic bone formation in genetically modified mice comprising the conditional allele induced in mice administered tamoxifen; an example of ectopic bone formation at the sternum is indicated in the right panel with white arrows. In the absence of tamoxifen (left panel), no ectopic bone formation is detected.
Figure 5:
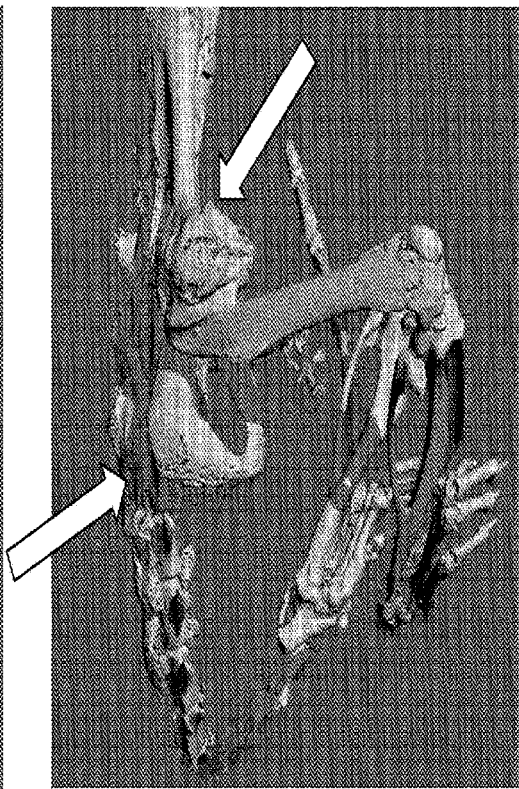
Figure 6:
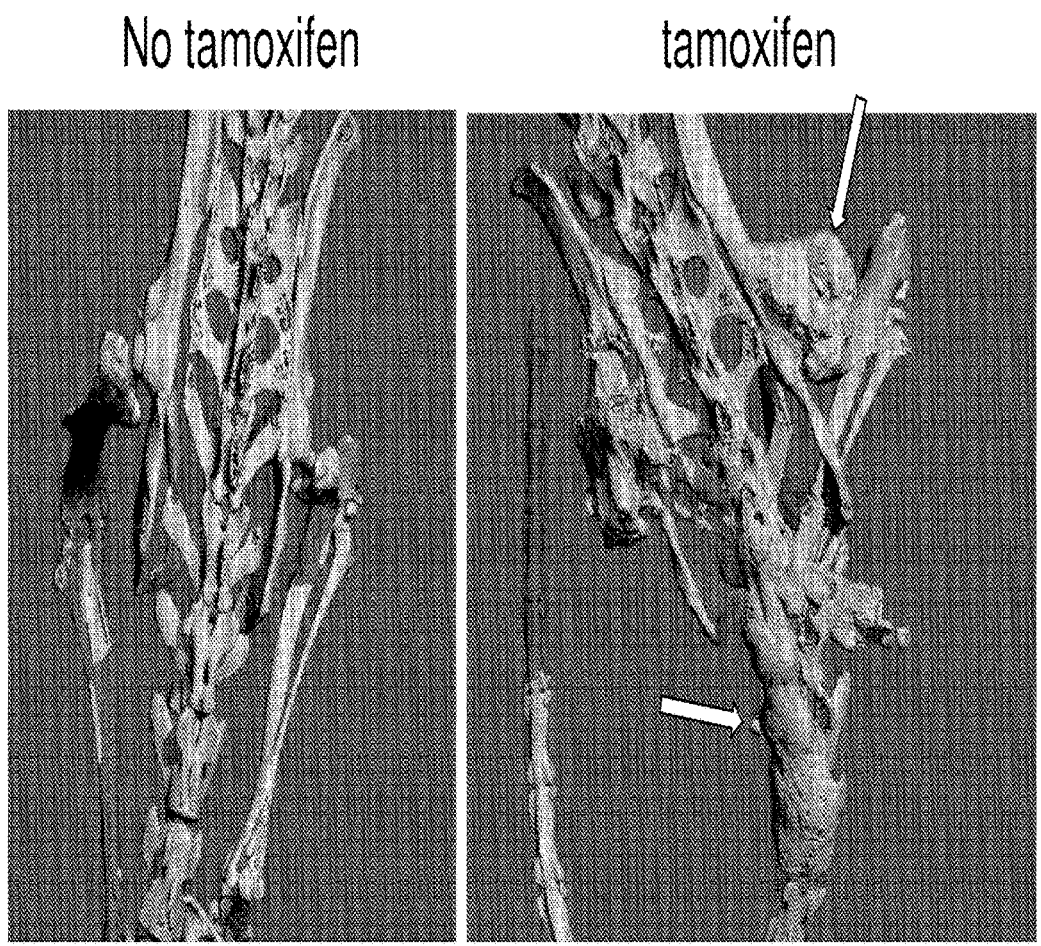
FIG. 6 provides yet another illustration of ectopic bone formation in genetically modified mice comprising the conditional allele induced in mice administered tamoxifen; an example of ectopic bone formation at the sternum is indicated in the right panel with white arrows. In the absence of tamoxifen (left panel), no ectopic bone formation is detected.
Figure 7:
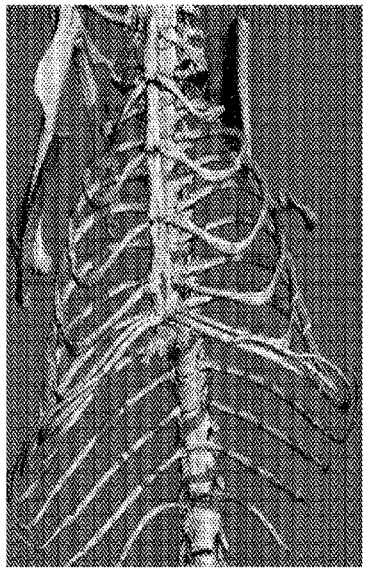
FIG. 7 illustrates control mice (left panels, ID 840095); and ectopic bone formation in genetically modified mice comprising the conditional allele induced in mice administered tamoxifen (Tamoxifen #2, ID:845202); top right panel shows ectopic bone formatoin at the sternebra; bottom right panel shows ectopic bone formation at the hip joint and the caudal vertebrae.
Figure 7:
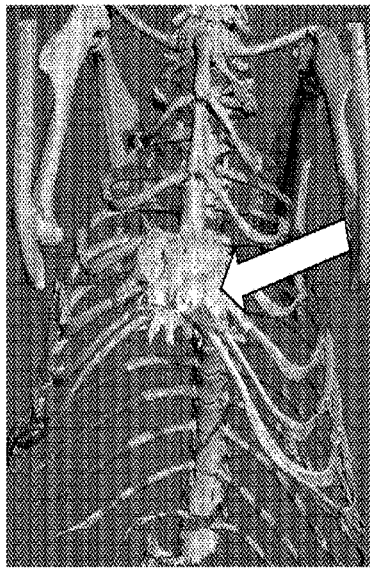
Figure 7:
Figure 7:
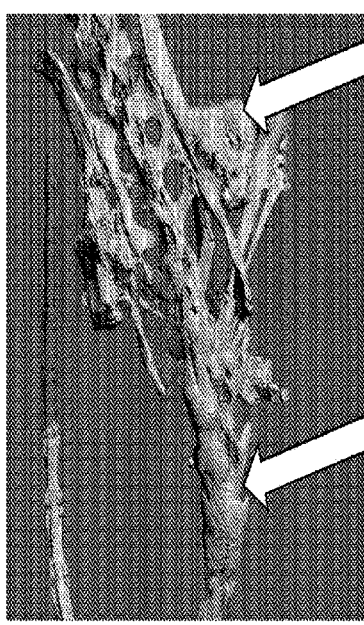
Figure 8:
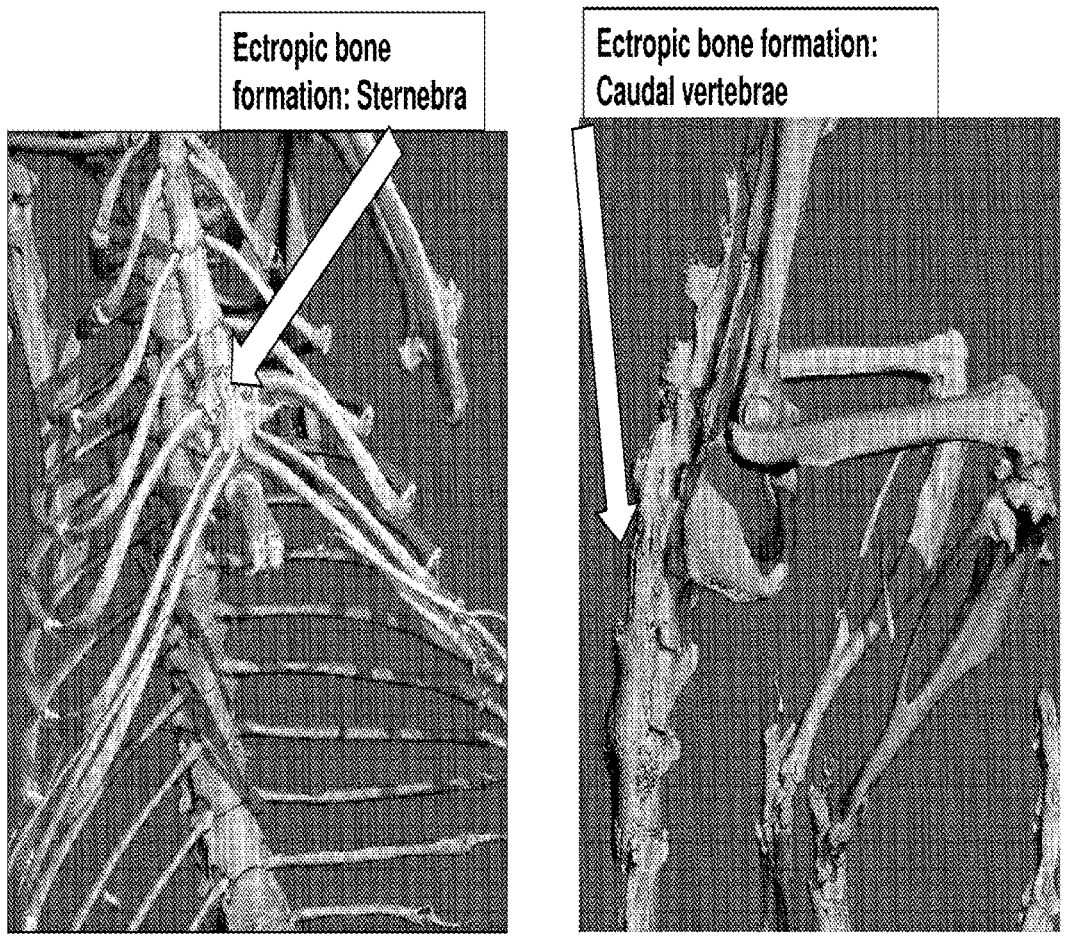
FIG. 8 illustrates ectopic bone formation at the sternebra (left panel) and the caudal vertebrae (right panel) for genetically modified mice comprising the conditional allele induced in mice administered tamoxifen (Tamoxifen #3, ID:915546).

FIEx employs a pair of mutant Lox sites—referred to as a FIEx array—that are recognized by the same recombinase—Cre—but which to do not react with one another, and laid out in an A–B/[A–B] configuration, where the "[A–B]" is in the opposite strand with respect to "A–B", to enable inversion of the DNA sequence flanked by the arrays. In its published embodiment, FIEx utilized sites LoxP and Lox511. Less known, however, is that in the presence of Cre a low level of recombination takes place between LoxP and Lox511. Therefore, different combinations of Lox site variants were tested, and the LoxP-Lox2372 combination were selected for the conditional allele described herein, because these two sites did not exhibit any cross-reactivity. An additional feature of FIEx is that the sequence that is contained within each array—i.e., between the LoxP and Lox2372 sites of each array—will be deleted upon action by Cre. The engineering of the allele of the invention (Acvr1$^{[R206H]COIN}$ allele) takes into account these two properties of FIEx. One embodiment of an conditional allele is illustrated in FIG. 2.

Mouse Acvr1 displays a variety of splice variants (e.g., 201, 202, 001, 003, 004). exon 5, which is mutated in FOP, is shared by all protein-coding splice variants of Acvr1. In one embodiment, the genetically modified mouse comprises a modification of exon 5 of an isoform selected from the group consisting of 201, 202, 001, 003, and 004.

The Acvr1$^{[R206H]COIN}$ allele was engineered by placing the mutant version of the R206-encoding exon of mouse Acvr1 (ENSMUSE00001021301) in the antisense strand, so that it is not incorporated into Acvr1's transcript. As the sequence encoded by exon 5 is required for Acvr1 function, this necessitated that an exon encoding for the wild type exon 5's sequence is also incorporated into the design (exon 5 is shared by all protein-coding splice variants of Acvr1). Furthermore, since exons are not recognized as such without accessory intronic sequences, both upstream and downstream of the exon had to be incorporated into both mutant and wild type R206-encoding exon. However, doing so would generate a large inverted repeat, and such DNA structures are inherently prone to recombination both during the genetic engineering steps required to build the targeting vector as well as post-targeting, in vivo (Holkers, M. et al. (2012) Nonspaced inverted DNA repeats are potential targets for homology-directed gene repair in mammalian cells, Nucleic Acids Res. 40:1984-1999). Furthermore, if the wild type mouse sequence of the R206-encoding exon and the upstream and downstream intronic sequence associated with it were retained intact, and precede the mutant exon, then this wild type region could act as a homology arm and be utilized during targeting in the mouse ES cells, thereby resulting in exclusion of the mutated exon from the targeted allele. Therefore, in order to address all these concerns the Acvr1$^{[R206H]COIN}$ allele was designed in a manner such that:

(a) A large inverted repeat is avoided. To accomplish this, the R206-encoding exon (ENSMUSE00001021301) as well associated upstream and downstream intronic sequences were replaced with the corresponding region from human ACVR1.

(b) The wild type mouse sequence of the R206-encoding exon (ENSMUSE00001021301) is preserved at the protein level. Given that the mouse and human protein sequence respectively encoded by exons ENSMUSE00001021301 and ENSE00001009618 differ by one amino acid, the human ENSE00001009618 exon sequence was altered so as to match the mouse protein sequence of exon ENSMUSE00001021301.

(c) The introduced human sequence is removed in its entirety upon action with Cre. Therefore, in the "conditional-on" state—where the Acvr1$^{[R206H]}$ mutant gene is transcribed—no human sequences remain and hence any resulting phenotype cannot be attributed to the presence of extraneous sequence.

More specifically, the region bounded by nucleotides 58474046 to 58474368 in mmuAcvr1 (i.e., nucleotides 58474046 to 58474368 of mouse Chromosome 2) where replaced with nucleotides 15863048 to 158630803 of hsaACVR1 (i.e., nucleotides 15863048 to 158630803 of human Chromosome 2), in a manner such that the introduced sequence, which includes hsaACVR1 exon ENSE00001009618 is transcribed as part of the resulting modified Acvr1$^{[R206H]COIN}$ locus. In addition, the coding sequence of the first amino acid of human exon ENSE00001009618 was replaced from aspartic acid (D) to glutamic acid (E) to correspond at the protein level to the exactly the same protein sequence as that encoded by mouse exon ENSMUSE00001021301. (This introduced human sequence is referred to hereafter as hsa_e5+.) Therefore, prior to inversion of the COIN element (mutated exon ENSMUSE00001021301 and associated upstream and downstream intronic sequences—see below), the resulting locus, Acvr1$^{[R206H]COIN}$, should function as wild type.

The R206H mutation was modeled by mutating exon ENSMUSE00001021301 in the corresponding position, by altering the codon defined by nucleotides 5847419 to 58474200 from CGC (coding for arginine) to CAC (coding for histidine). The resulting mutant exon, along with flanking intronic sequences upstream and downstream were placed 3' to hsa_e5+ and in the antisense strand of mmuAcvr1, replacing nucleotides 58473775 to 58473879 of mmuAcvr1 in order to also create a small deletion and accommodate LOA probes (Gomez-Rodriguez, J. et al. (2008) Advantages of q-PCR as a method of screening for gene targeting in mammalian cells using conventional and whole BAC-based constructs, Nucleic Acids Res. 36:e117; Valenzuela, D. et al. (2003) High-throughput engineering of the mouse genome coupled with high-resolution expression analysis, Nat. Biotech. 21:652-659). (This introduced mutated mouse sequence is hereafter referred to as mmu_e5R206H+.)

In order to enable Cre-dependent inversion of the mmu_e5R206H+ and simultaneous deletion of hsa_e5+, a combination of FIEx like Lox arrays where used such that:

(a) hsa_e5+ is preceded by a LoxP site, and followed by a Lox2372 site. In this respect, hsa_e5+ is contained with the 5' LoxP-Lox2372 FIEx-like array.

(b) mmu_e5R206H+ is followed by the 3' LoxP-Lox2372 FIEx-like array, but this array is engineered such that it is in a mirror image configuration to 5' LoxP-Lox2372 FIEx-like array. This enables permanent inversion of mmu_e5R206H+ into the sense strand by Cre.

When the resulting allele, Acvr1$^{[R206H]COIN}$ is exposed to Cre, the hsa_e5+ will be deleted and the mmu_e5R206H+ will be inverted into the sense strand. As a result, Acvr1$^{[R206H]}$ will be expressed in place of Acvr1.

Genetically modified mice were genotypes employing a loss of allele assay (see, e.g., Valenzuela et al., (2003), supra). Primers and probes were as shown in FIG. 12 (Table 5).

Phenotype of Acvr1$^{R206HCOIN/+}$ Mice

Acvr1$^{R206HCOIN/+}$ mice are phenotypically normal but develop FOP after activation of the R206H conditional mutation.

Based on published results with a non-conditional, simple knock-in Acvr1 R206H chimeric mouse (Chakkalakal et al., 2012) as well as the fact that FOP is an autosomal-dominant disorder (for a review see (Pignolo et al., 2011)), it was hypothesized that:

(a) Unlike the non-conditional Acvr1$^{R206H}$ allele (Chakkalakal et al., 2012), targeted ES cells for Acvr1$^{[R206H]COIN}$ will produce VELOCIMICE®, i.e., F0 mice that are entirely derived from the targeted ES cells (Poueymirou et al. (2007) F0 generation mice fully derived from gene-targeted embryonic stem cells allowing immediate phenotypic analyses, Nat. Biotech. 25:91-99).

(b) Unlike the non-conditional Acvr1$^{R206H/+}$ chimeric mice (Chakkalakal et al., 2012), F0 Acvr1$^{[R206H]COIN/+}$ mice will be phenotypically normal, and will transmit the Acvr1$^{[R206]COIN}$ allele to the next generation.

(c) Upon inversion of mutant exon bearing the R206H mutation into the sense strand—an action mediated by Cre recombinase—cells that have been converted to the Acvr1$^{[R206H]INV/+}$ genotype will express the mutant Acvr1$^{[R206H]}$ allele as well as the wild-type allele, mirroring the situation in FOP patients. Along the same lines, the resulting Acvr1$^{[R206H]INV/+}$ mice should overtime develop FOP-like symptoms.

All of these hypotheses were born out. For example, ES cell clone 1649C-A2 gave rise to 16 VELOCIMICE® out of 19 mice generated using that clone (Table 1).

TABLE 1

Acvr1$^{[R206H]COIN/+}$ ES Cells Give Rise Mainly to Male F0 Mice Wholly Derived from Donor ES Cells

| Mouse ID | Chimerism (%) |
| --- | --- |
| 1649C-A2/758470 | 100 |
| 1649C-A2/758471 | 100 |
| 1649C-A2/758472 | 100 |
| 1649C-A2/758473 | 100 |
| 1649C-A2/758474 | 100 |
| 1649C-A2/758475 | 100 |
| 1649C-A2/758476 | 100 |
| 1649C-A2/758477 | 100 |
| 1649C-A2/758478 | 100 |
| 1649C-A2/758479 | 100 |
| 1649C-A2/758480 | 100 |
| 1649C-A2/758481 | 100 |
| 1649C-A2/758482 | 100 |
| 1649C-A2/758483 | 100 |
| 1649C-A2/758484 | 100 |
| 1649C-A2/758485 | 100 |
| 1649C-A2/758486 | 80 |
| 1649C-A2/758487 | 70 |
| 1649C-A2/758488 | 30 |

Furthermore, these mice had no discernible phenotype and were able to reproduce and father Acvr1$^{[R206H]COIN/+}$ F1 generation mice (Table 2).

TABLE 2

F1 Mice Born to Acvr1$^{[R206H]COIN/+}$ F0 Fathers

| Clone Name/ID | Genotype | Gender |
| --- | --- | --- |
| 1649C-A2/2251A-C6/840095 | 1649 Het 2251 Het | M |
| 1649C-A2/2251A-C6/840098 | 1649 Het 2251 Het | M |
| 1649C-A2/2251A-C6/845202 | 1649 Het 2251 Het | M |
| 1649C-A2/2251A-C6/845203 | 1649 Het 2251 Het | F |
| 1649C-A2/2251A-C6/845204 | 1649 Het 2251 Het | F |
| 1649C-A2/2251A-C6/845205 | 1649 Het 2251 WT | F |
| 1649C-A2/2251A-C6/845809 | 1649 Het 2251 WT | F |
| 1649C-A2/2251A-C6/863706 | 1649 Het 2251 WT | F |
| 1649C-A2/2251A-C6/863707 | 1649 Het 2251 WT | F |
| 1649C-A2/2251A-C6/863713 | 1649 Het 2251 Het | M |
| 1649C-A2/2251A-C6/863714 | 1649 Het 2251 WT | M |
| 1649C-A2/2251A-C6/897113 | 1649 Het 2251 WT | F |
| 1649C-A2/2251A-C6/897115 | 1649 Het 2251 WT | F |
| 1649C-A2/2251A-C6/897117 | 1649 Het 2251 Het | F |
| 1649C-A2/2251A-C6/904065 | 1649 Het 2251 WT | M |
| 1649C-A2/2251A-C6/904067 | 1649 Het 2251 Het | M |
| 1649C-A2/2251A-C6/904069 | 1649 Het 2251 WT | F |
| 1649C-A2/2251A-C6/904783 | 1649 Het 2251 WT | M |
| 1649C-A2/2251A-C6/904785 | 1649 Het 2251 WT | F |
| 1649C-A2/2251A-C6/907167 | 1649 Het 2251 WT | F |

TABLE 2-continued

F1 Mice Born to Acvr1[R206H]COIN/+ F0 Fathers

| Clone Name/ID | Genotype | Gender |
|---|---|---|
| 1649C-A2/2251A-C6/915545 | 1649 Het 2251 WT | M |
| 1649C-A2/2251A-C6/915546 | 1649 Het 2251 Het | M |
| 1649C-A2/2251A-C6/964988 | 1649 Het 2251 Het | F |
| 1649C-A2/2251A-C6/964989 | 1649 Het 2251 Het | F |

F1 generation Acvr1[R206H]COIN/+; Gt(ROSA26)Sor$^{CreERt2/+}$ mice born to Acvr1[R206H]COIN/+ F0 fathers From a phenotypic standpoint, Acvr1[R206H]COIN/+ mice appear normal, and display no discernible phenotypes. The same applies to Acvr1[R206H]COIN/+; Gt(ROSA26)Sor$^{CreERt2/+}$ mice, which in addition to the Acvr1[R206H]COIN allele also carry a CreER$^{T2}$ transgene knocked into the Gt(ROSA26)Sor locus. This allows ubiquitous expression of an inactive version of Cre, one that is dependent upon tamoxifen for activation (Feil et al. (1997) Regulation of Cre recombinase activity by mutated estrogen receptor ligand-binding domains, Biochem. Biophys. Res. Commun. 237: 752-757). This enables the activation of Cre at a specific point in time, and hence not only allows bypassing the embryonic lethality experienced with the conventional Acvr1[R206H] knock-in of but also empowers the investigator to choose the time of activation of the Acvr1[R206H] expression in the corresponding mice.

In order to investigate whether Acvr1[R206H]COIN/+; Gt(ROSA26)Sor$^{CreERt2/+}$ mice develop FOP after exposure to tamoxifen, we generated a small cohort and treated it with tamoxifen starting at approximately one year of age (Table 3); it is notable that by this age mice have completed their development, and therefore no modeling or development-related mechanisms are at play and therefore cannot contribute to the pathological process. Delivery of tamoxifen was by injection into the peritoneum using a 10 mg/mL solution in corn oil. Injections were performed daily for 8 days. In three mice (Mice 1, 2, and 3 of Table 3), a small piece of muscle was resected to induce injury.

TABLE 3

Protocol for Cre-Mediated Tamoxifen-Dependent Activation of Acvr1[R206H]COIN Allele in Acvr1[R206H]COIN/+; Gt(ROSA26)$^{CreERt2/+}$ Mice

| Mouse | Mouse ID | Daily Injection | Start Day | Age at Start (yrs) | End Day | Sacrifice Day | Sacrifice Age (yrs) |
|---|---|---|---|---|---|---|---|
| 1 | 840095 | corn oil | 1 | 0.9 | 8 | 143 | 1.3 |
| 2 | 845202 | TAM* | 1 | 0.9 | 8 | 143 | 1.3 |
| 3 | 915546 | TAM | 1 | 0.56 | 8 | 143 | 1.0 |

TABLE 3-continued

Protocol for Cre-Mediated Tamoxifen-Dependent Activation of Acvr1[R206H]COIN Allele in Acvr1[R206H]COIN/+; Gt(ROSA26)$^{CreERt2/+}$ Mice

| Mouse | Mouse ID | Daily Injection | Start Day | Age at Start (yrs) | End Day | Sacrifice Day | Sacrifice Age (yrs) |
|---|---|---|---|---|---|---|---|
| 4 | 904067 | TAM | 1 | 0.61 | 8 | 143 | 1.0 |
| 5 | 840098 | TAM | 1 | 0.90 | 8 | 143 | 1.3 |
| 6 | 863713 | TAM | 1 | 0.80 | 8 | 143 | 1.2 |

TAM: tamoxifen

All but one of the tamoxifen-treated mice developed ectopic ossification, mirroring what has been observed in FOP (Table 4). Although the specific cell type(s) that might be contributing to the disease process were not determined in this experiment due to the fact that the expression of CreER$^{t2}$ is ubiquitous (a property imparted by the fact that it is expressed from the Gt(ROSA26)Sor locus), one of the important aspects of this work is that it removes the developmental aspects of FOP (which are not those most important to FOP's pathology, as they do not contribute to the devastating loss in quality of life the FOP patients experience), and shows that the ectopic bone formation that is the major post-natal hallmark of FOP pathology is independent of developmental processes.

TABLE 4

Four Acvr1[R206H]COIN/+; Gt(ROSA26)$^{CreERt2/+}$ Mice Exposed to Tamoxifen Develop FOP-Like Skeletal Pathology

| Mouse | Mouse ID | Ectopic Bone Formation |
|---|---|---|
| 1 | 840095 | None* |
| 2 | 845202 | sternebra, hip joint, caudal vertebrae |
| 3 | 915546 | sternebra, hip joint, caudal vertebrae |
| 4 | 904067 | none |
| 5 | 840098 | sternebra |
| 6 | 863713 | sternebra, knee joint |

*Treated with corn oil (vehicle) only, not tamoxifen

Figure 9:
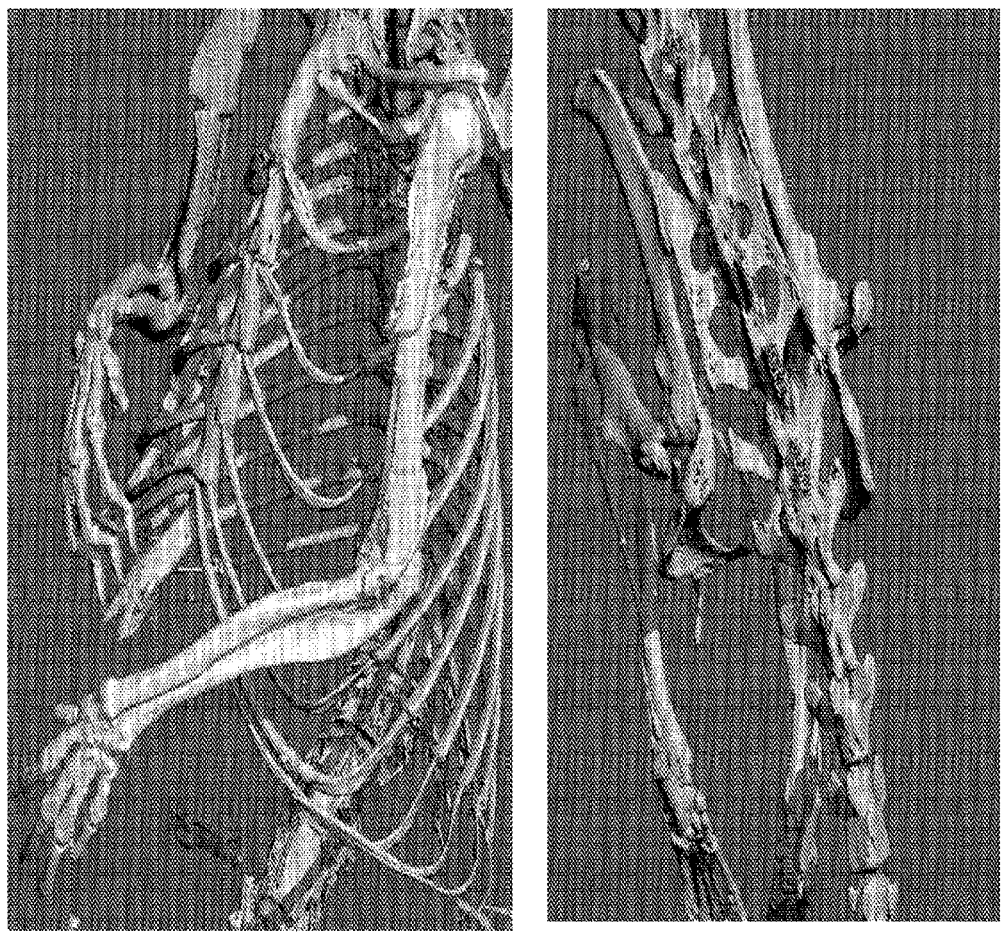
FIG. 9 illustrates the absence of ectopic bone formation in genetically modified mouse comprising the conditional allele, induced with tamoxifen (Tamoxifen #4, ID:904067).
Figure 10:
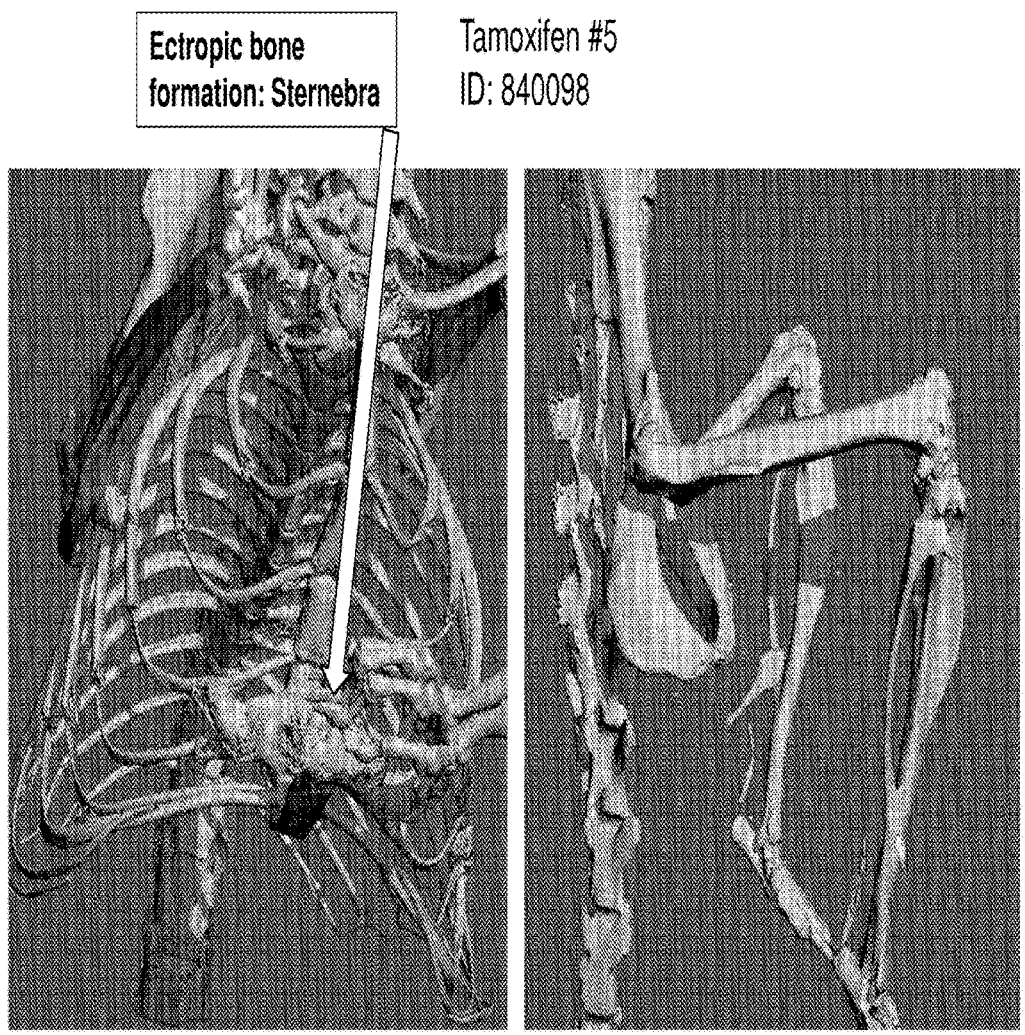
FIG. 10 illustrates ectopic bone formation at the sternebra (left panel) in genetically modified mice comprising the conditional allele induced by administration of tamoxifen (Tamoxifen #5, ID:840098).
Figure 11:
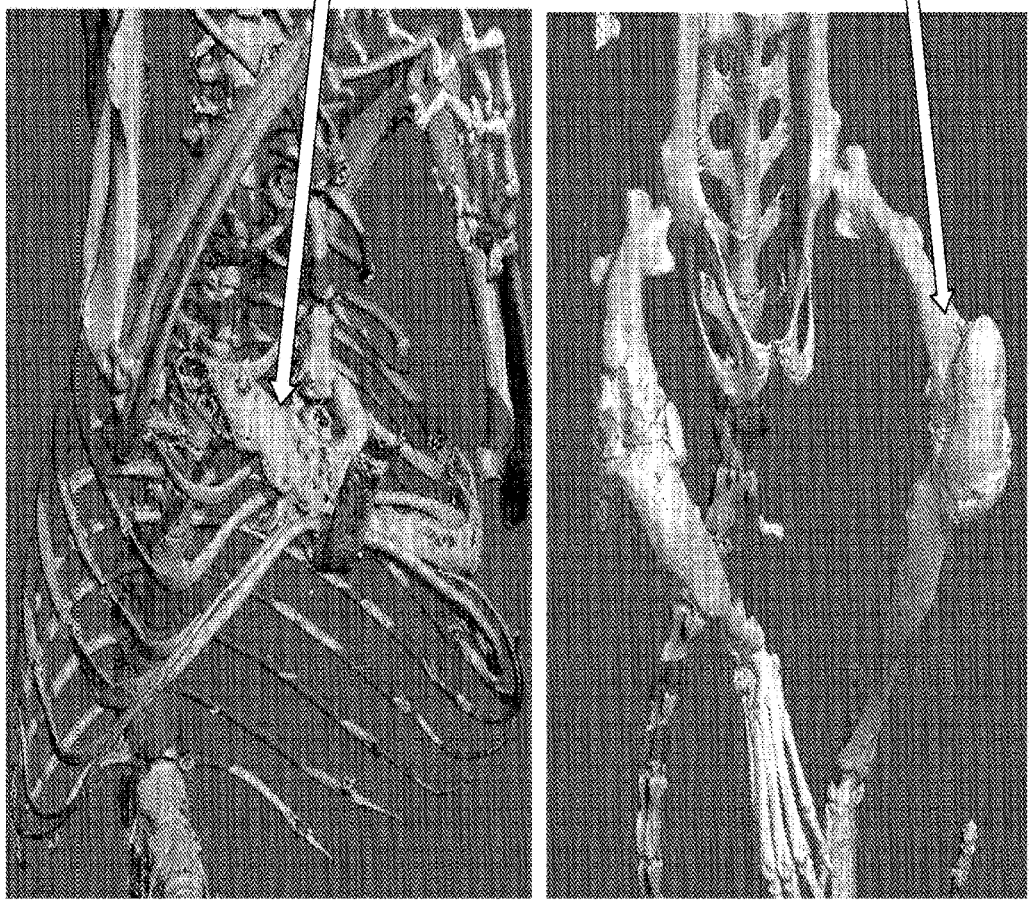
FIG. 11 illustrates ectopic bone formation at the sternebra (left panel) and knee joint (right panel) in genetically modified mice comprising the conditional allele induced by administration of tamoxifen (Tamoxifen #6, ID:863713).

Ectopic ossification is shown in images of genetically modified mice as described herein exposed to tamoxifen (which display ectopic ossification). Mice that are genetically modified as described herein but not exposed to tamoxifen do not display ectopic ossification See, e.g., FIG. 3, FIG. 4, FIG. 5, FIG. 6, FIG. 7, FIG. 8, FIG. 10, and FIG. 11. Ectopic ossification is demonstrated in a variety of body areas. As shown in FIG. 9, one mouse showed no apparent ectopic bone formation.

We claim:

1. A method for making a progeny mouse comprising: breeding a first mouse whose genome comprises a modified mouse Activin A receptor type 1 (Acvr1) gene comprising: i) a human exon 5 of the Acvr1 gene encoding glutamic acid at the first codon instead of aspartic acid in sense orientation flanked upstream and downstream by first pair of recombination recognition sites; and ii) a mutant exon 5 of a mouse Acvr1 gene comprising an R206H mutation in antisense orientation flanked upstream and downstream by second pair of recombination recognition sites that are different than the first pair of recombination recognition sites; wherein the first and second recombination recognition sites are oriented so that a recombinase can invert the mutant exon 5 into sense orientation, delete the human exon 5, and allow a mutant Acvr1 comprising the mutant exon 5 to be expressed resulting in ectopic bone formation, with a second mouse whose genome comprises a nucleic acid sequence encoding a inducible recombinase, such that a progeny mouse whose genome comprises the modified mouse Acvr1 gene and the nucleic acid sequence encoding the inducible recombinase is obtained, wherein the progeny mouse is capable of forming ectopic bone upon inducing expression of the recombinase.

2. The method according to claim 1, wherein the inducible recombinase comprises inducible Cre recombinase.

3. The method according to claim 2, wherein the inducible Cre recombinase comprises tamoxifen-inducible Cre-ER$^T$ or Cre-ER$^{T2}$ recombinase.

4. The method according to claim 3, wherein the inducible recombinase is expressed in a cell in the progeny mouse comprising the modified mouse Acvr1 gene.

5. The method according to claim 3, further comprising inducing the Cre-ER$^T$ or Cre-ER$^{T2}$ recombinase in the progeny mouse, wherein the Cre-ER$^T$ or Cre-ER$^{T2}$ recombinase inverts the mouse Acvr1 gene exon 5 into sense orientation and deletes the human Acvr1 gene exon 5, thereby producing the recombined modified mouse Acvr1 gene encoding the R206H variation, and allowing the recombined modified mouse Acvr1 gene to be expressed resulting in ectopic bone formation.

6. The method according to claim 2, wherein the inducible recombinase is expressed in a cell in the progeny mouse comprising the modified mouse Acvr1 gene.

7. The method according to claim 2, further comprising inducing the Cre recombinase in the progeny mouse, wherein the recombinase inverts the mouse Acvr1 gene exon 5 into sense orientation and deletes the human Acvr1 gene exon 5, thereby producing the recombined modified mouse Acvr1 gene encoding the R206H variation, and allowing the recombined modified mouse Acvr1 gene to be expressed resulting in ectopic bone formation.

8. The method according to claim 1, wherein the inducible recombinase is expressed in a cell in the progeny mouse comprising the modified mouse Acvr1 gene.

9. The method according to claim 1, wherein the progeny mouse is heterozygous for the modified mouse Acvr1 gene.

10. The method according to claim 1, wherein the progeny mouse is homozygous for the modified mouse Acvr1 gene.

11. A progeny mouse made by the method of claim 1, wherein the progeny mouse has a genome comprising the modified mouse Acvr1 gene and the nucleic acid sequence encoding the inducible recombinase, and wherein the progeny mouse is capable of forming ectopic bone upon inducing expression of the recombinase.

12. The progeny mouse according to claim 11, wherein the inducible recombinase comprises inducible Cre recombinase.

13. The progeny mouse according to claim 12, wherein the inducible Cre recombinase comprises tamoxifen-inducible Cre-ER$^T$ or Cre-ER$^{T2}$ recombinase.

14. The progeny mouse according to claim 13, wherein the inducible recombinase is expressed in a cell in the progeny mouse comprising the modified Acvr1 gene.

15. The progeny mouse according to claim 12, wherein the inducible recombinase is expressed in a cell in the progeny mouse comprising the modified Acvr1 gene.

16. The progeny mouse according to claim 11, wherein the inducible recombinase is expressed in a cell in the progeny mouse comprising the modified Acvr1 gene.

17. The progeny mouse according to claim 11, wherein the progeny mouse is heterozygous for the modified Acvr1 gene.

18. The progeny mouse according to claim 11, wherein the progeny mouse is homozygous for the modified Acvr1 gene.

19. A progeny mouse made by the method of claim 1, in which recombinase expression has been induced and wherein the progeny mouse forms ectopic bone.

20. The progeny mouse according to claim 19, wherein the inducible recombinase comprises inducible Cre recombinase.

21. The progeny mouse according to claim 19, wherein the inducible Cre recombinase comprises tamoxifen-inducible Cre-ER$^T$ or Cre-ER$^{T2}$ recombinase.

* * * * *

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Synthesized

<400> SEQUENCE: 1
ggctgactga tctgaaggaa atgg

```
<210> SEQ ID NO 2
<211> LENGTH: 24
<212> TYPE: DNA
<213> ORGANISM: Artificial Sequence
<220> FEATURE:
<223> OTHER INFORMATION: Synthesized

<400> SEQUENCE: 2
tgaaggaaat gggcttctgg atag                                              24

<210> SEQ ID NO 3
<211> LENGTH: 23
<212> TYPE: DNA
<213> ORGANISM: Artificial Sequence
<220> FEATURE:
<223> OTHER INFORMATION: Synthesized

<400> SEQUENCE: 3
agaggaagga gacgctaaga atc                                               23

<210> SEQ ID NO 4
<211> LENGTH: 25
<212> TYPE: DNA
<213> ORGANISM: Artificial Sequence
<220> FEATURE:
<223> OTHER INFORMATION: Synthesized

<400> SEQUENCE: 4
catactcact cttcctgtta gagga                                             25

<210> SEQ ID NO 5
<211> LENGTH: 26
<212> TYPE: DNA
<213> ORGANISM: Artificial Sequence
<220> FEATURE:
<223> OTHER INFORMATION: Synthesized

<400> SEQUENCE: 5
tctggatagt aaggtcagtt gctgcg                                            26

<210> SEQ ID NO 6
<211> LENGTH: 23
<212> TYPE: DNA
<213> ORGANISM: Artificial Sequence
<220> FEATURE:
<223> OTHER INFORMATION: Synthesized

<400> SEQUENCE: 6
aaggtcagtt gctgcgtctt ccc                                               23
```